United States Patent
Massen

(10) Patent No.: US 7,298,889 B2
(45) Date of Patent: Nov. 20, 2007

(54) METHOD AND ASSEMBLY FOR THE PHOTOGRAMMETRIC DETECTION OF THE 3-D SHAPE OF AN OBJECT

(75) Inventor: Robert Massen, Ohningen-Wangen (DE)

(73) Assignee: corpus.e AG, Stuttgart (DE)

( * ) Notice: Subject to any disclaimer, the term of this patent is extended or adjusted under 35 U.S.C. 154(b) by 754 days.

(21) Appl. No.: 10/276,914

(22) PCT Filed: May 23, 2001

(86) PCT No.: PCT/EP01/05935

§ 371 (c)(1),
(2), (4) Date: Nov. 20, 2002

(87) PCT Pub. No.: WO01/92824

PCT Pub. Date: Dec. 6, 2001

(65) Prior Publication Data
US 2003/0137510 A1   Jul. 24, 2003

(30) Foreign Application Priority Data
May 27, 2000   (DE) ................................ 100 25 922

(51) Int. Cl.
*G06K 9/00* (2006.01)
(52) U.S. Cl. .................................................. 382/154
(58) Field of Classification Search .................. None
See application file for complete search history.

(56) References Cited

U.S. PATENT DOCUMENTS

| | | | | |
|---|---|---|---|---|
| 3,510,210 A | * | 5/1970 | Haney | 352/39 |
| 4,745,290 A | * | 5/1988 | Frankel et al. | 250/559.17 |
| 5,828,770 A | * | 10/1998 | Leis et al. | 382/103 |
| 5,889,879 A | * | 3/1999 | Tsai et al. | 382/123 |
| 6,363,169 B1 | * | 3/2002 | Ritter et al. | 382/154 |
| 6,434,278 B1 | * | 8/2002 | Hashimoto | 382/285 |
| 6,580,821 B1 | * | 6/2003 | Roy | 382/154 |
| 6,724,930 B1 | * | 4/2004 | Kosaka et al. | 382/154 |
| 2003/0012408 A1 | * | 1/2003 | Bouguet et al. | 382/103 |

FOREIGN PATENT DOCUMENTS

EP   0 760 622 B1   3/1997

* cited by examiner

*Primary Examiner*—Matthew C. Bella
*Assistant Examiner*—Alex Liew
(74) *Attorney, Agent, or Firm*—Stuart J. Friedman

(57) ABSTRACT

For an automatic detection of the 3D shape of objects by photogrammetry, the background of the photogrammetric point markers is characterized by area markers which comprise a plurality of point markers and have a characteristic optical configuration that is expressed, e.g., in the color, shape, texture, or gray level of the surface area of the area marker. During the image processing of the photogrammetric images taken of an object, first the area markers and then the point markers present in the respective area markers are referenced in relation to one another. Instead of using area markers, a further embodiment uses constellation-type point marker arrangements, which are first referenced before the individual point markers forming the constellations are referenced. The method is particularly useful for the 3D detection of body parts which have been clad with an envelope marked in accordance with the invention, prior to the photogrammetric evaluation.

25 Claims, 6 Drawing Sheets

METHOD AND ASSEMBLY FOR THE PHOTOGRAMMETRIC DETECTION OF THE 3-D SHAPE OF AN OBJECT

The invention relates to methods and arrangements for the photogrammetric detection of the 3D shape of an object.

Contactless detection of the 3D shape of bodies and objects such as motor vehicle bodies, human body parts and the like is an important measuring method in quality control, in reverse engineering, in the generation of numerical 3D models of physically existing bodies, etc.

A number of different methods are known in literature and on the market, which are based either on stripe projection, laser line projection, laser transit time measurement, or photogrammetry, and some are based on a combination of different methods.

The so-called passive methods of short-range photogrammetry are especially cost-effective since merely calibrated cameras or digital cameras are needed here, but no expensive projection units or precisely calibrated mechanical structures are required.

One typical representative of this group is the "Photo-Modeler" software of the EOS company (see the Internet website www.photomodeler.com). This software allows to develop the numerical 3D model of an object from different images of the object which overlap as far as the captured parts of the object are concerned. In doing so, however, the positions of markers stuck onto the body to be measured or of distinct features such as corners or lines of such body need to be manually marked on the screen on the different 2D photographs by the user using a mouse and need to be referenced in pairs, that is, corresponding markers need to be associated with each other manually in the different photographs. Where a dense sequence of XYZ coordinate values is required, several hundred to thousand such assignment processes need to be carried out manually. This is not only extremely tedious, but also prone to errors, since it is almost impossible to assign without errors many markers that look the same.

It is further known from photogrammetry to use markers with encoded point numbers (encoded point markers) which bear a pattern with an encoded point number. For this purpose, point encodings are used that are distributed on a line or ring or over an area and that are arranged around the measuring point proper. The identity of the encoded point markers can be recognized automatically by an image processing unit, whereupon the points in the images can then be associated in pairs automatically.

These encoded point markers, however, need to be fairly large in order to accommodate a code such as, e.g., a radial bar code, a two-dimensional point code or the like. As a rule, each marker requires an individual code. This in turn prevents this method from being applied in the case of small bodies requiring many markers since due to the restricted spatial conditions, these point markers can no longer be applied in sufficient numbers.

Further known are photogrammetric methods which can do without encoded markers and iteratively determine the association of markers that look the same. But these methods require accurately calibrated cameras, are very lengthy, and demand of the user good knowledge of the photogrammetric boundary conditions, in particular the appropriate imaging positions and the necessary amount of overlap, for the iterative solution methods to converge.

Patent specification EP 0 760 622, "Sensing Process and Arrangement for the Three-Dimensional Shape in Space of Bodies or Body Parts", Inventor and Applicant: Robert Massen, describes a method and an arrangement by means of which body parts to be digitized can be marked in a simple and cost-effective way by covering the body part with a tight-fitting elastic envelope featuring markers adapted to be evaluated photogrammetrically. As an example, this patent specification discusses the marking of a human foot to generate 3D models for the production of prostheses or made-to-measure shoes. This method allows, in a simple and cost-effective way, to apply a large number of markers and thereby to provide the basis for obtaining dense XYZ coordinates by photogrammetry. This, however, does not yet solve the problem of simple automatic registration of markers from the overlapping regions of the different images.

The object of the present invention is to provide methods and arrangements for the photogrammetric detection of the 3D shape of an object, which are suitable for automatic referencing of photogrammetric markers and for high-resolution digitizing of objects, bodies or body parts, and which more particularly overcome the above-mentioned drawbacks occurring in photogrammetric methods that use encoded point markers.

This object is attained by a method of detecting the 3D shape of an object by photogrammetry, comprising the steps of providing point markers and one or more area markers on the surface of the object, each area marker comprising a plurality of point markers, forming a background of the point markers, and having a surface area having a characteristic optical configuration; taking a plurality of photogrammetric images of the object from respective different views; performing an image processing of the images, in which first the area markers respectively corresponding in the images are associated with one another using their characteristic optical configuration, and then the point markers comprised by the area markers and respectively corresponding in the images are associated with one another with the aid of the area marker association; and, using the point marker association, determining the 3D shape of the object by means of a photogrammetric evaluation process.

Furthermore, this object is attained by a method of detecting the 3D shape of an object by photogrammetry, comprising the steps of providing point markers on the surface of the object in such a manner that groups of a plurality of point markers are formed, the point markers in a group being arranged in relation to one another such that a characteristic point marker arrangement is produced; taking a plurality of photogrammetric images of the object from respective different views; performing an image processing of the images, in which first the characteristic point marker arrangements respectively corresponding in the images are associated with one another and then, with the aid of such association, the point markers comprised by the characteristic point marker arrangements and respectively corresponding in the images are associated with one another; and, using the point marker association, determining the 3D shape of the object by means of a photogrammetric evaluation process.

In addition, the object of the invention is attained by an arrangement for detecting the 3D shape of an object by photogrammetry, comprising an imaging system for obtaining photogrammetric images of different views of the object and a system for measuring and evaluating the images and for determining the 3D shape of the object, which is characterized in that the arrangement further includes point markers and one or more area markers provided on the surface of the object, each area marker comprising a plurality of point markers, forming a background of the point markers, and having a surface area having a characteristic optical configuration.

Finally, the object is attained in accordance with the invention by an arrangement for detecting the 3D shape of an object by photogrammetry, comprising an imaging system for obtaining photogrammetric images of different views of the object and a system for measuring and evaluating the images and for determining the 3D shape of the object, which is characterized in that the arrangement further includes point markers which are provided on the surface of the object in such a manner that groups of a plurality of point markers are formed, the point markers in a group being arranged in relation to one another such that a characteristic point marker arrangement is produced.

The methods and arrangements in accordance with the invention result in the following advantageous effect:

The inclusion of characteristically configured background areas behind the point markers for referencing, and the combination of noncoded point markers to form characteristic superordinate point marker arrangements allows a convenient and precise automated referencing of points even when the object whose 3D shape is to be determined by photogrammetry is small and/or requires a multitude of point markers for a sufficient determination of the 3D shape by means of photogrammetric methods.

Advantageous further developments of the invention are characterized in the dependent claims.

Further features and advantages of the invention will be apparent from the following description of an embodiment with reference to the drawings, in which:

FIG. 1 shows two possible embodiments of the encoded point markers mentioned in the introduction to the specification, that are part of the prior art.

The invention will now be explained by way of example, but not in a limiting sense, with reference to the employment of optical detection of the 3D shape of a human foot for obtaining the 3D data required for an automated selection of shapes of shoes that fit or suitable shoe lasts.

It is assumed here, likewise by way of example, but not in a limiting sense, that the foot is clad in a tight-fitting, elastic envelope according to the above-mentioned patent EP 0 760 622, which has on its surface noncoded point markers that look the same, in the form of small crosses.

As an example, the idea underlying a preferred embodiment of the invention will be discussed, that is, the idea of background marking involving a coloration, carried out region by region, of the background of the point markers. Since it is not possible to print color pictures in patent specifications, the different coloration is represented in the Figures by different black-and-white textures.

Figure 2:
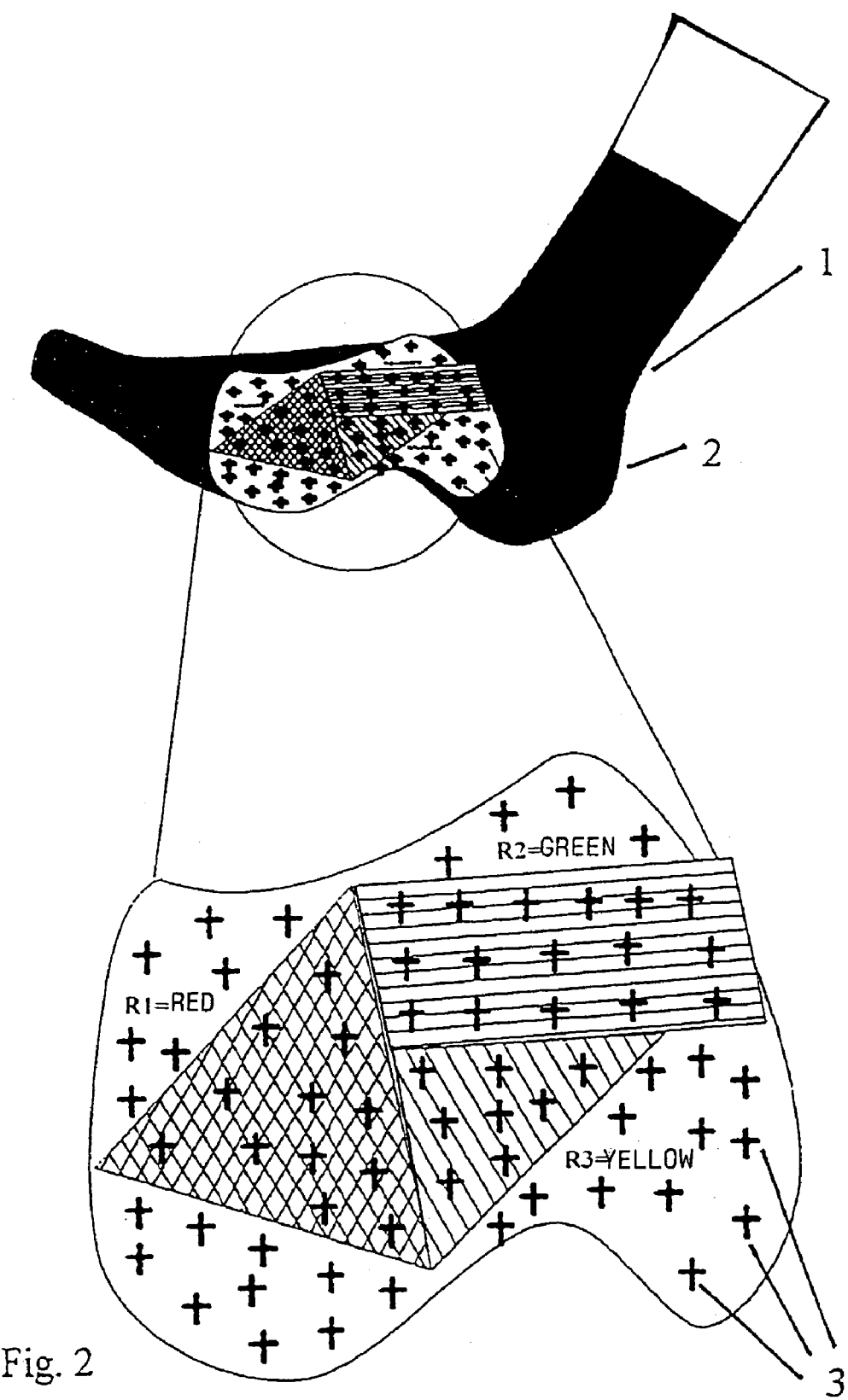
FIG. 2 illustrates an embodiment of the invention in the case of a human foot that is covered by an envelope provided with point markers and colored area markers.

FIG. 2 shows a human foot 1, which is clad in a tight-fitting, elastic envelope 2. The envelope 2 has on its surface a large number of identically looking photogrammetric point markers 3 in the form of small crosses.

The intersection point of the two lines of the point markers represents an XY coordinate in the particular image observed, that can be determined using methods of two-dimensional image processing and can also be exactly determined as a two-dimensional coordinate in relation to the coordinate system of the particular image even in the case of different imaging angles, perspective distortions or the like. When digital cameras are used for image taking, for example, the coordinate system on which each image is based is dictated by the line and column structure of the sensor array and by the piercing point of the optical axis.

Figure 1:
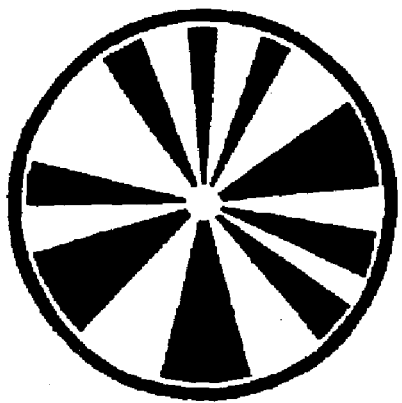
FIG. 1 shows two different encoded point markers that are part of the prior art.
Figure 1:

As an example, only three regions, R1, R2 and R3 with the different background colors RED, GREEN and YELLOW are reproduced in FIG. 1. It is known to a person of ordinary skill in the art of image processing that color cameras can be used for automatic segmenting of such color regions with the aid of the colors occurring, which the system has been previously trained to recognize, i.e. such color regions can be automatically recognized and distinguished from each other. Methods of this type are described, for example, in German Patent DE 36 39 636 C2, "Automatic Inspection of Lengths of Textile Fabric", Inventor and Applicant: Robert Massen.

It is further known that such color segmenting can be made to be especially robust and independent of the viewing angle if color classifiers are employed that are independent of the brightness (which is dependent on the viewing angle). This can be done by, e.g., classification of each pixel using the color tone following conversion of the RGB color signals to the HSI color range (hue, saturation, intensity).

Figure 3:
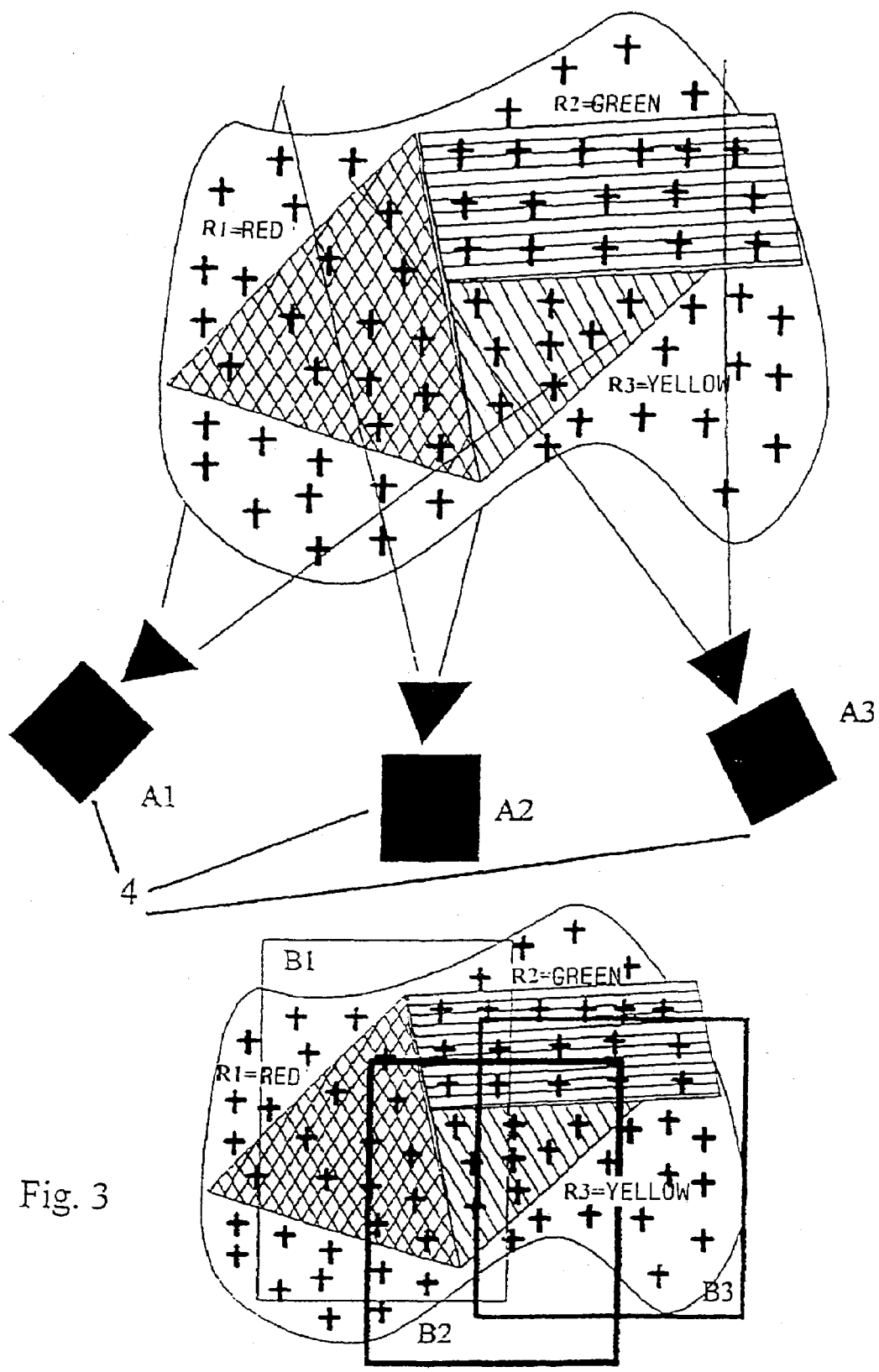
FIGS. 3, 4 and 5 are diagrammatic illustrations showing how the photogrammetric evaluation is effected with the aid of the point and area markers illustrated in FIG. 2.

As is shown clearly in FIG. 3, as an example it is assumed that images are taken of the surface of the body to be digitized as defined by the three regions R1, R2 and R3 from three different imaging positions, A1, A2 and A3, using a digital camera 4. The respective three two-dimensional images, B1, B2 and B3, each show overlapping sectors of the body surface.

Figure 4:
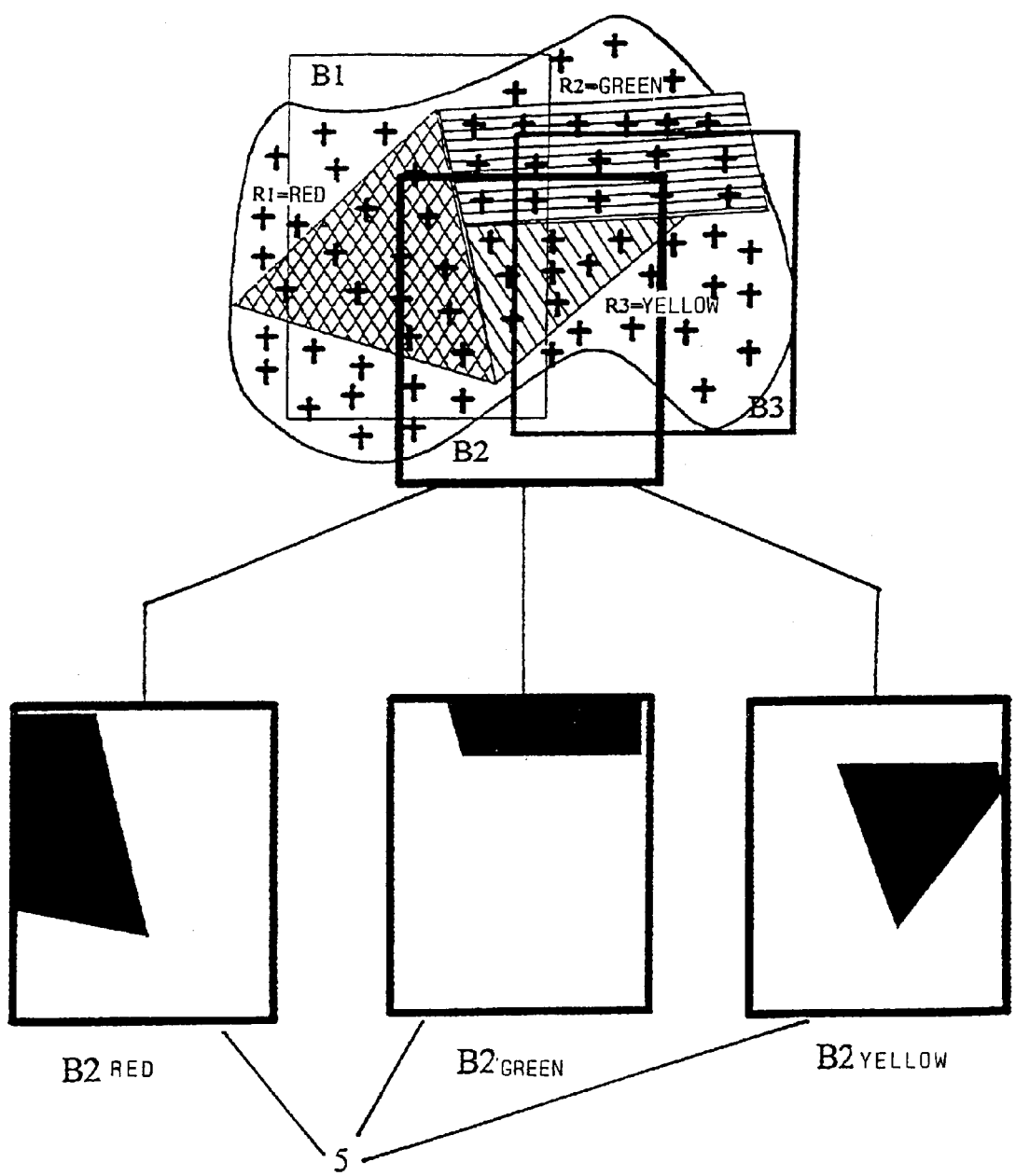

By a pixel-by-pixel color classification of all three images into the colors RED, GREEN and YELLOW, each of the three images, B1, B2 and B3, can be automatically decomposed into three so-called color class images 5 (in FIG. 4), B1-> B1RED,B1GREEN,B1YELLOW
B2-> B2RED,B2GREEN,B2YELLOW
B3-> B3RED,B3GREEN,B3YELLOW, as is shown in FIG. 4 using the region B2 as an example. Accordingly, an automatic association of all regions that match in pairs has now already occurred, that is, while the photogrammetric markers have not yet been referenced, the background regions, R1, R2, and R3 of these markers have already been referenced.

The background regions, each of which comprises a plurality of point markers, will also be referred to as areas markers below because of their planar configuration, by analogy with the known point markers.

According to the invention, the point markers within two referenced regions (area markers) are automatically associated with each other by a comparison of their positions in relation to the region boundaries and/or by an evaluation of the distinguishable figures formed by a plurality of point markers and/or by minor alterations of their shapes.

Figure 5:
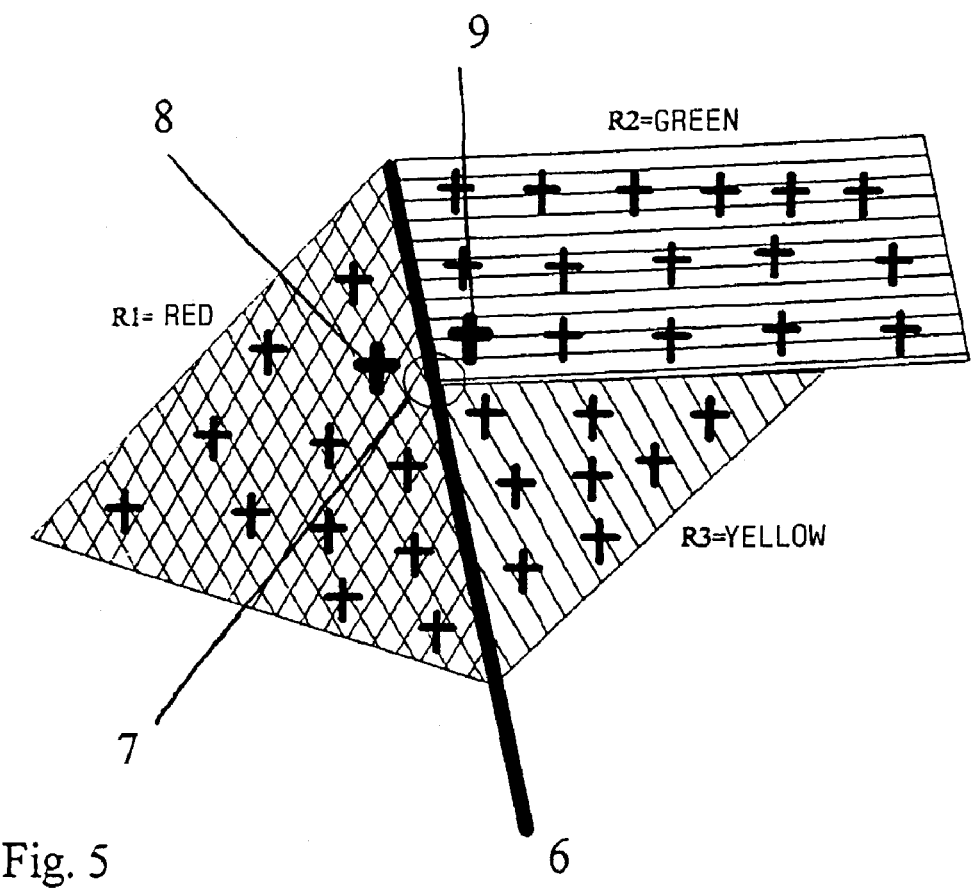

FIG. 5 shows, by way of example, how the photogrammetric point markers situated directly at the region boundaries can be associated with each other based on the information contained in the color class images about these boundaries and the corners formed by regions.

As an example, one side of the triangular red region R1 is assumed to adjoin the likewise triangular yellow region R3 and the green region R2 having the form of a parallelogram.

Forming along the lateral edge 6 observed is furthermore a "boundary between three countries", i.e. a distinct point 7 where three area markers (regions) marked with three different colors meet. This point may be easily found by comparing all color class images with a neighborhood operator in the two overlapping images B1 and B2. One of ordinary skill in the art of color image processing is familiar with such methods. Once the coordinate of this point in the two images B1 and B2 observed has been established, the noncoded photogrammetric point markers, shown here by the small black-and-white crosses 8 and 9 as an example, can easily be associated with one another using classical search methods, beginning at this starting point, parallel to the color region boundary and within the corresponding regions.

A further advantage of the color-coded regions is the possibility to check automatically after each image is taken whether the degree of overlap of two images taken is sufficiently large. The degree of overlap results from the number of pixels with the identical color in each image.

In addition to the area marking of the background regions by color, texture or similar features, the shape of the background region may also be made to bear information that facilitates automated referencing. For instance, owing to their pointed corners, triangular regions are suited to be easily recognized and associated by means of methods of 2D image processing.

Figure 6:
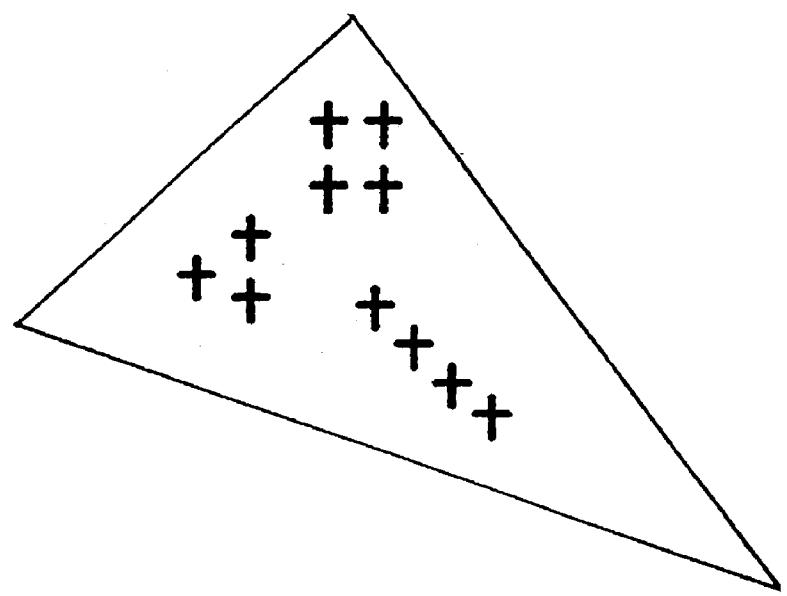
FIG. 6 shows a further embodiment of the invention, in which the point markers are combined in groups having characteristic point marker arrangements in the form of a constellation.

Aside from the automated referencing of the photogrammetric point markers based on their position in relation to the region boundaries, other features of these noncoded point markers may also be used. As shown in FIG. 6, according to the invention the photogrammetric point markers are for example grouped to form characteristic point marker arrangements similar to "constellations", i.e. the relative position of several noncoded point markers within a region is selected such that automatically identifiable geometric shapes are formed, such as triangles, parallelepipeds, oblong structures, etc. In particular, those structures are of advantage which are invariant with respect to affine image transformations such as translation, rotation, elongation, extension, perspective distortion. Such image distortions are always produced when an image sector is taken from two different imaging positions. Such group arrangements are always possible since the position of the photogrammetric markers may be freely selected within limits, in particular in the case of bodies having continuously curved surfaces.

Figure 7:
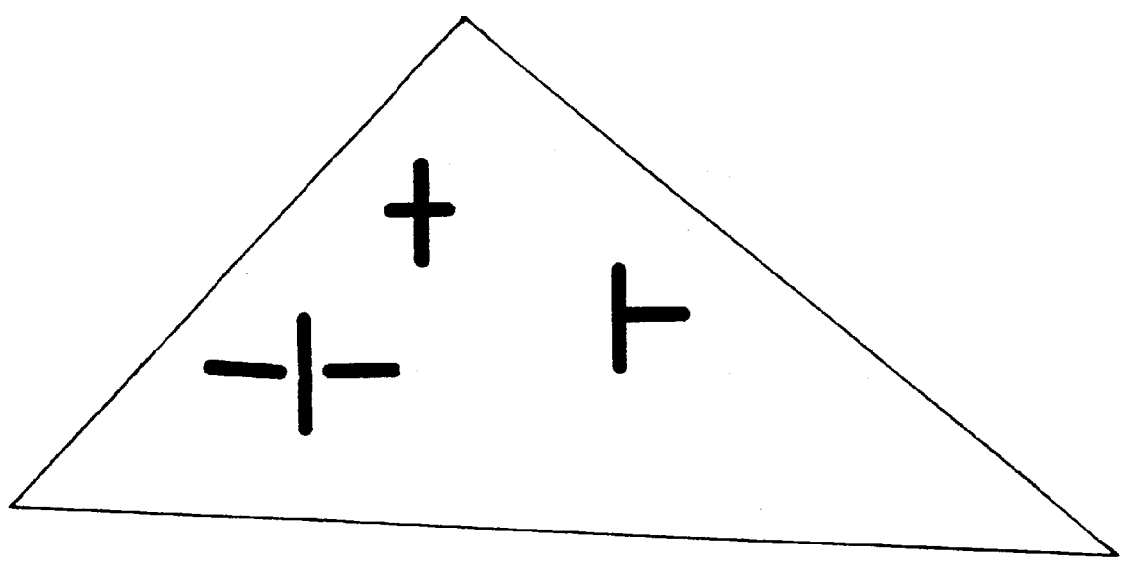
FIG. 7 is a diagrammatic view of point markers, as are used in a preferred embodiment of the invention.

It is further possible to make the photogrammetric point markers within one region identifiable by slightly modifying their shapes. This may be done, for example, by varying the length or appearance of the bars, as shown in FIG. 7. This type of encoding differs substantially from the known methods of encoding by means of bar codes or the like. In the method according to the invention, only the point markers within one region are marked differently; it is not necessary for all point markers covering the entire body to be identifiable. The coding may therefore be very simple and only needs to distinguish between few marker patterns. For this reason, small markings may be used.

By combining the individual methods of referencing the photogrammetric point markers within an area marker (region), the markers contained in identical regions from two or more overlapping images may be easily associated with one another using methods of two-dimensional image processing and pattern recognition, even in the case of larger color regions.

Accordingly, the two method steps of (a) referencing the background regions associated with one another on the basis of planar features, such as color, texture, degree of polarization, NIR reflection, degree of polarization, and the like, (b) referencing the noncoded photogrammetric point markers within one region on the basis of their positions in relation to the regions, their grouping structures, and simple features of shape allow to perform a complete automatic photogrammetric evaluation of a body or body part marked in accordance with the invention.

It is, of course, also possible according to the invention to combine the method as described with conventionally encoded photogrammetric point markers, as are illustrated, e.g., in FIG. 1.

In the embodiment of the invention using the area markers, various modifications are conceivable. What is always important is that the area markers exhibit a particular optical configuration, so that different area markers can be distinguished from one another in image processing. This optical configuration may consist in, e.g., a characteristic shape, a characteristic color, a characteristic gray level, a characteristic texture, i.e. a characteristic pattern or a characteristic structure, a characteristic gloss, a surface coating applied to the surface of the area markers and having a characteristic degree of polarization, or a characteristic combination of the above-listed optical configuration features. The area markers may furthermore be characterized in their optical configuration in that they emit radiation either in the visible or in the invisible part of the spectrum.

Also, the area markers need not necessarily be applied to an envelope. They can just as well be provided directly on the object. Moreover, self-adhesive films may, for example, be attached to the object, the films having the point and area markers applied thereon. Finally, it is also conceivable that the point and area markers are projected onto the surface of the object. The same applies of course to the point markers in the case of the embodiment involving the constellation-type point marker arrangements.

The point markers may also have different shapes, and they do not necessarily need to consist of crosses. Instead, they may, e.g., consist of the intersection points of a net.

The invention claimed is:

1. A method of detecting and for high-resolution digitizing of the 3D shape of an object, by photogrammetry using a multitude of point markers on said object, comprising the steps of:

applying at least two area markers on the surface of the object, each of said area markers having a surface with a characteristic optical configuration different from the other area markers;

providing a plurality of said point markers in each area marker, whereby said characteristic optical configuration of said area markers forms a background for the point markers;

taking a plurality of photogrammetric images of the object from respective different views;

performing an image processing of the images, in which first the area markers in the images are automatically recognized by their respective characteristic optical configuration;

then, the area markers respectively corresponding in the images are automatically associated with one another using their characteristic optical configuration, and for each set of associated area markers, automatically associating the point markers provided within each of said associated area markers and respectively corresponding in the images with one another determining the 2D coordinates for each of the associated point markers: and performing a photogrammetric evaluation process for determining the 3D shape of the object using the said 2D coordinates of the multitude of associated point markers.

2. The method as claimed in claim 1, wherein the characteristic optical configuration of the surface area of the area markers consists in a characteristic shape, a characteristic color, a characteristic gray level, a characteristic texture, i.e. a characteristic pattern or a characteristic structure, a characteristic gloss, a surface coating applied to the surface of the area markers and having a characteristic degree of polarization, or a characteristic combination of the above-listed optical configuration features.

3. The method as claimed in claim 1, wherein the area markers are characterized in their optical configuration in that they emit radiation either in the visible or in the invisible part of the spectrum.

4. The method as claimed in claim 1, wherein the point and area markers are provided on the object by pulling an elastic envelope having the point and area markers applied thereto over the object.

5. The method as claimed in any of claims 1 to 3, wherein the point and area markers are provided on the object by sticking self-adhesive films having the point and area markers applied thereto onto the surface of the object.

6. The method as claimed in any of claims 1 to 3, wherein the point and area markers are provided on the object by projecting the point and area markers onto the surface of the object.

7. The method as claimed in claim 1, wherein the point markers comprised by an area marker are provided in a specific arrangement in relation to one another and to the peripheral line of the surface area of the area marker.

8. The method as claimed in claim 7, wherein the point marker association is performed with the aid of the area marker association in such a way that the point markers appearing in different images are associated with one another using their geometric position in relation to the peripheral lines of the areas formed by the area markers and/or using characteristic point marker arrangements formed by the point markers within the area markers.

9. A method of detecting and for high-resolution digitizing of the 3D shape of an object by photogrammetry using a multitude of point markers on said object, comprising the steps of:

applying said multitude of point markers on the surface of the object;

said point markers forming groups of a plurality of said point markers;

in each of said groups, arranging said point markers within a group in relation to one another for producing a characteristic point marker arrangement different from the characteristic point marker arrangement of the other groups;

taking a plurality of photogrammetric images of the object from respective different views;

performing an image processing of the images, in which first, said groups of a plurality of said point markers in the images are automatically recognized by their respective characteristic arrangement;

then, the groups respectively corresponding in the images are automatically associated with one another using their characteristic point marker arrangements;

for each set of said associated groups, automatically associating the point markers comprised by the associated characteristic point marker arrangements and respectively corresponding in the images with one another;

determining the 2D coordinates for each of the associated point markers; and performing a photogrammetric evaluation process for determining the 3D shape of the object using the said 2D coordinates of the multitude of associated point markers.

10. The method as claimed in claim 9, wherein the point markers are provided on the object by pulling an elastic envelope having the point markers applied thereto over the object.

11. The method as claimed in claim 9, wherein the point markers are provided on the object by sticking self-adhesive films having the point markers applied thereto onto the surface of the object.

12. The method as claimed in claim 9, wherein the point markers are provided on the object by projecting them onto the surface of the object.

13. The method as claimed in claim 1, wherein the point markers are noncoded.

14. The method as claimed in claim 1, wherein the point markers consist of crosses.

15. The method as claimed in claim 1, wherein the point markers consist of the intersection points of a net.

16. An arrangement for detecting and for high-resolution digitizing the 3D shape of an object by photogrammetry using a multitude of point markers on said object, comprising:

an imaging system for obtaining photogrammetric images of different views of the object; and a system for measuring and evaluating the images and for determining the 3D shape of the object, wherein the arrangement further includes at least two area markers on the surface of the object, each of said area markers having a surface with a characteristic optical configuration different from the other area markers; and a plurality of said point markers comprised in each area marker, said characteristic optical configuration of said area markers forming a background for said point markers;

the system being configured for performing an image processing of the images, in which first the area markers in the images are automatically recognized by their respective characteristic optical configuration;

then, the area markers respectively corresponding in the images are automatically associated with one another using their characteristic optical configuration, and p2 for each set of associated area markers, the point markers provided within each of said associated area markers and respectively corresponding in the images are automatically associated with one another;

the 2D coordinates for each of the associated point markers are determined: and a photogrammetric evaluation process for determining the 3D shape of the object using said 2D coordinates of the multitude of associated point markers is performed.

17. The arrangement as claimed in claim 16, further including an elastic envelope having the point markers and the one area marker or the plurality of area markers applied thereto and being designed such that it can be pulled over the object, adapting to the shape of the object.

18. The arrangement as claimed in claim 16, further including one or more self-adhesive films having the point markers and the one area marker or the plurality of area markers applied thereto and being designed such that when stuck on the surface of the object, they are in tight-fitting contact with the object.

19. The arrangement as claimed in claim 16, further comprising a projection system designed to be used for projecting the point markers and the one area marker or the plurality of area markers onto the object.

20. An arrangement for detecting and for high-resolution digitizing of the 3D shape of an object by photogrammetry using a multitude of point markers on said object, comprising
   an imaging system for obtaining photogrammetric images of different views of the object; and
   a system for measuring and evaluating the images and for determining the 3D shape of the object, wherein the arrangement further includes groups of said point markers, each group being formed by a plurality of said point markers;
   in each of said groups, said point markers within a group are arranged in relation to one another for producing a characteristic point marker arrangement different from the characteristic point marker arrangement of the other groups;
   the system being configured for performing an image processing of the images, in which
      first said groups of a. plurality of said point markers in the images are automatically recognized by their respective characteristic arrangement:
   then, the groups respectively corresponding in the images are automatically associated with one another using their characteristic point marker arrangements:
      for each set of said set of said associated groups, the point markers comprised by the associated characteristic point marker arrangements and respectively corresponding in the images are automatically associated with one another;
      the 2D coordinates for each of the associated point markers is determined; and
   a photogrammetric evaluation process is performed for determining the 3D shape of the object using said 2D coordinates of the multitude of associated point markers.

21. The arrangement as claimed in claim 20, further including an elastic envelope having the point markers applied thereto and being designed such that it can be pulled over the object, adapting to the shape of the object.

22. The arrangement as claimed in claim 20, further including one or more self-adhesive films having the point markers applied thereto and being designed such that when stuck on the surface of the object, they are in tight-fitting contact with the object.

23. The arrangement as claimed in claim 20, further comprising a projection system designed to be used for projecting the point markers onto the object.

24. The method as claimed in claim 1, wherein the object is a body part of a human being.

25. The arrangement as claimed in claims 16 or 20, wherein the object is a body part of a human being.

* * * * *